(12) United States Patent
Yachia et al.

(10) Patent No.: US 8,282,678 B2
(45) Date of Patent: Oct. 9, 2012

(54) ENDOLUMINAL LINING

(75) Inventors: Daniel Yachia, Herzliya Pituach (IL); Ronnie Levy, Zur Yigal (IL)

(73) Assignee: Allium Medical Solutions Ltd., Caesarea Industrial Park-South (IL)

( * ) Notice: Subject to any disclaimer, the term of this patent is extended or adjusted under 35 U.S.C. 154(b) by 555 days.

(21) Appl. No.: 10/292,753

(22) Filed: Nov. 13, 2002

(65) Prior Publication Data

US 2004/0093065 A1    May 13, 2004

(51) Int. Cl.
 *A61F 2/82* (2006.01)
(52) U.S. Cl. ....................................... 623/1.13
(58) Field of Classification Search ............ 623/1.2, 623/1.15, 1.22, 1.13, 23.64–23.66, 23.69–23.71, 623/1.16, 1.44, 1.3, 1.32, 1.37
See application file for complete search history.

(56) References Cited

U.S. PATENT DOCUMENTS

| | | | |
|---|---|---|---|
| 4,886,062 A | 12/1989 | Wiktor | |
| 5,123,917 A * | 6/1992 | Lee | 623/22.26 |
| 5,383,892 A | 1/1995 | Cardon et al. | |
| 5,514,178 A | 5/1996 | Torchio | |
| 5,549,663 A * | 8/1996 | Cottone, Jr. | 623/1.22 |
| 5,651,174 A | 7/1997 | Schwartz et al. | |
| 5,662,713 A * | 9/1997 | Andersen et al. | 128/898 |
| 5,665,115 A * | 9/1997 | Cragg | 623/1.13 |
| 5,667,486 A * | 9/1997 | Mikulich et al. | 604/8 |
| 5,741,333 A | 4/1998 | Frid | |
| 5,766,209 A | 6/1998 | Devonec | |
| 5,830,179 A * | 11/1998 | Mikus et al. | 604/517 |
| 5,861,036 A * | 1/1999 | Godin | 623/23.64 |
| 6,042,597 A | 3/2000 | Kveen et al. | |
| 6,159,238 A * | 12/2000 | Killion et al. | 623/1.11 |
| 6,200,335 B1 | 3/2001 | Igaki | |
| 6,270,524 B1 | 8/2001 | Kim | |
| 6,273,911 B1 | 8/2001 | Cox et al. | |
| 6,305,436 B1 * | 10/2001 | Andersen et al. | 140/107 |
| 6,379,379 B1 * | 4/2002 | Wang | 623/1.15 |
| 2005/0277928 A1 | 12/2005 | Boschert | |
| 2006/0122706 A1 | 6/2006 | Lo | |
| 2006/0122709 A1 | 6/2006 | Devonec | |

FOREIGN PATENT DOCUMENTS

| | | |
|---|---|---|
| FR | 2 745 172 | 8/1997 |
| JP | A-1-145076 | 6/1989 |
| JP | A-05-507215 | 10/1993 |
| JP | A-06-007454 | 1/1994 |
| JP | A-07-136282 | 5/1995 |
| JP | A-08-509394 | 10/1996 |
| JP | A-08-336597 | 12/1996 |
| JP | A-09-099058 | 4/1997 |

(Continued)

OTHER PUBLICATIONS

Japanese Office Action, Japanese Patent Office, p. 7.

(Continued)

*Primary Examiner* — Ryan Severson
(74) *Attorney, Agent, or Firm* — Oliff & Berridge, PLC

(57) ABSTRACT

A cylindrical lining for insertion into a body lumen having a fluctuating caliber, such as a pulsating artery, peristaltic organ, or a lumen adjacent to a sphincter. The lining has a radial resistance less than a radial force applied to it by the lumen as the caliber of the lumen fluctuates so as to allow the lining to continuously conform to the shape of the lumen.

20 Claims, 4 Drawing Sheets

FOREIGN PATENT DOCUMENTS

| | | |
|---|---|---|
| JP | A-09-285548 | 11/1997 |
| JP | A-10-506297 | 6/1998 |
| JP | A-11-347133 | 12/1999 |
| JP | A-2000-312721 | 11/2000 |
| JP | A-2002-500533 | 1/2002 |
| JP | A-2002-531169 | 9/2002 |
| JP | A-2002-532136 | 10/2002 |
| JP | A-2008-502428 | 1/2008 |
| JP | A-2008-509899 | 4/2008 |
| WO | WO 92/00043 | 1/1992 |
| WO | WO 98/43695 | 10/1998 |
| WO | WO 98/52497 | 11/1998 |
| WO | WO 99/56663 | 11/1999 |
| WO | WO 00/32137 | 6/2000 |
| WO | WO 01/89421 A2 | 11/2001 |
| WO | WO 03/017882 A2 | 3/2003 |

OTHER PUBLICATIONS

Translation of Japanese Office Action dated Mar. 30, 2010.
Japanese Office Action, Japanese Patent Office, p. 7, Aug. 25, 2009.

* cited by examiner

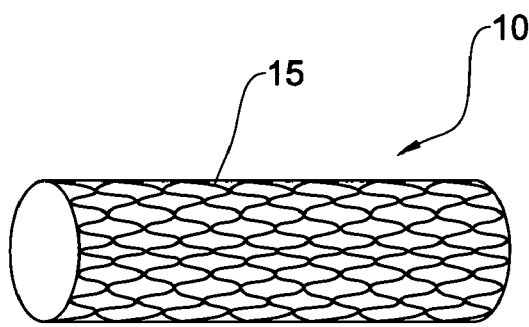
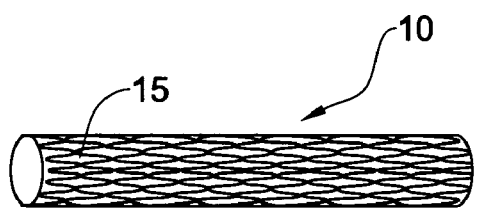
FIG. 1A
FIG. 1B
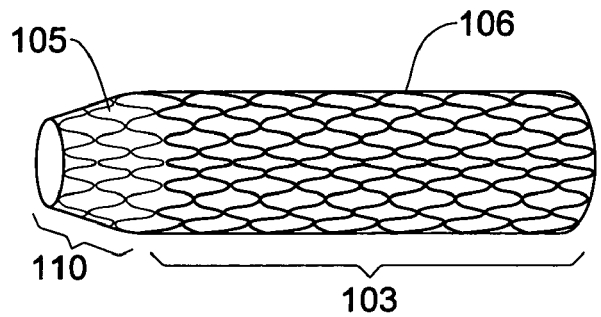
FIG. 2A
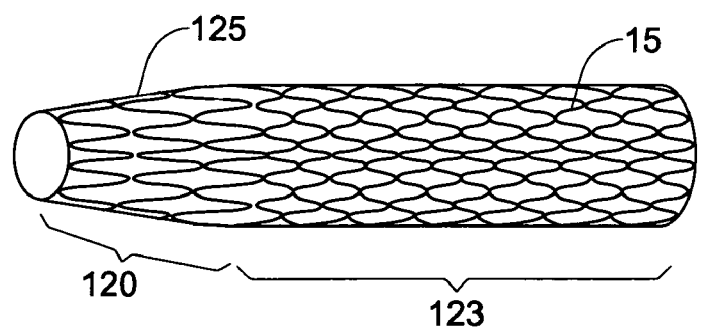
FIG. 2B
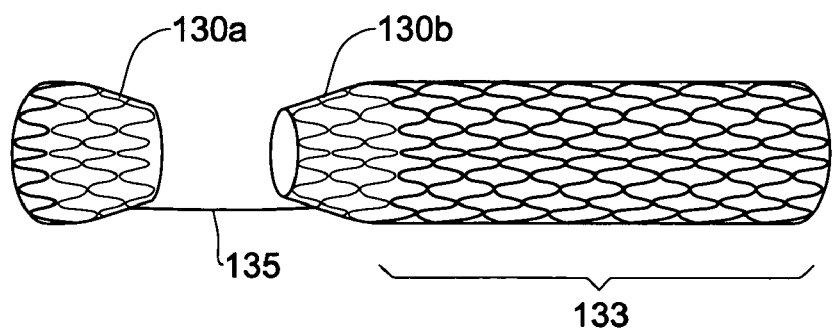
FIG. 3

ENDOLUMINAL LINING

FIELD OF THE INVENTION

This invention relates to medical devices for insertion into body cavities.

BACKGROUND OF THE INVENTION

Stents are endoluminal devices that are inserted into body lumens and expanded in order to maintain the patency of the lumen. It is known for example, to use a stent to maintain the patency of an artery, a urethra, or a gastrointestinal organ.

A stent is essentially a cylindrical device that can exist in two conformations. In the small caliber conformation, the stent is inserted into the body and delivered to the lumen to be treated. Once correctly positioned in the lumen, the stent is deployed by being brought into a large caliber in which it applies radially outward forces against the inner wall of the lumen. The stent is constructed so as to be able to withstand all radially inward forces applied to it by the lumen wall, so that the caliber of the stent does not change after deployment in the lumen.

A stent may be formed, for example, from an elastic material that is unstrained when the stent is in the large caliber conformation. The stent is then mechanically constrained to bring it into the small caliber conformation. This stent may be constrained in the small caliber conformation by inserting it into a restraining sleeve. After positioning in the body, the restraining sleeve is removed. Due to the elastic properties of the stent, the stent spontaneously transforms into the large caliber conformation.

It is also known to form a stent from a material that becomes plastic when strained. The stent is formed in the small caliber conformation in which it is unstrained. A balloon is inserted into the lumen of the stent. The stent is then positioned in the body and the balloon is inflated. This expands the stent into the large caliber conformation by causing a plastic deformation of the stent material.

It is further known to form a stent from a shape memory alloy, such as Nitinol™. A shape memory alloy may exist in two states: a state in which it is super-elastic (the austenitic state) and a state in which it is soft (the martensitic state). The alloy in the austenitic state is formed into a stent in its large caliber conformation. The alloy is then brought into the martensitic state either by cooling the alloy or straining it. In the martensitic state, the alloy is deformed into the small caliber conformation in which it is delivered to the lumen to be treated. After positioning, the alloy is brought into the austenitic state by heating the alloy. In the austenitic state, the stent regains the large caliber conformation due to the shape-memory properties of the alloy.

It is further known to form a stent from a biostable or biodegradable elastic shape memory polymer. The shape memory capability of these polymers allows stents made of these materials to be inserted through small openings and then enlarging their caliber by an increase in temperature. The shape memory effect of polymers is a physical property exhibited best by amorphous polymers whose glass transition temperature is marginally higher than room temperature and whose transition from glass to rubber is particularly sharp. In this case, strain energy can be stored in the polymer by mechanical deformation (e.g. by stretching) followed by cooling. Recovery of the shape memory is exhibited upon reheating the material above the temperature to which it was cooled, allowing a return of the stretched polymer chains to more equilibrium, coiled structures.

There are many body lumens whose caliber fluctuates dynamically over time. Such body lumens include, for example, a pulsating artery, a peristaltic digestive tract organ or a portion of a lumen adjacent to a sphincter.

A sphincter is a formation of muscle tissue encircling a portion of a body lumen. Contraction of the sphincter occludes the lumen to prevent the passage of material in the lumen from one side of the sphincter to the other. For example, the gastro-esophageal sphincter is located at the junction between the esophagus and the stomach. When closed it prevents the stomach contents from refluxing into the esophagus. The pyloric sphincter is located at the junction between the stomach and the small intestine. When closed, it prevents the stomach contents from entering the small intestine. The voluntary urethral sphincter is located below the prostatic urethra and controls the flow of urine from the urinary bladder.

It is often desired to place a stent in a body lumen whose diameter changes dynamically over time. For example, it may be desired to place a stent in a region of a body lumen adjacent to a sphincter. Thus, it may be desired to place a stent in the prostatic urethra near the voluntary urethral sphincter. It may also be desired to place a stent in the esophagus adjacent to the gastro-esophageal sphincter, to place a stent in the duodenum adjacent to the pyloric sphincter, or to place a stent in the common bile duct adjacent to the Oddi sphincter. Placing a cylindrical stent in a body lumen adjacent to a sphincter often interferes with the proper functioning of the sphincter. The radially outward forces exerted on the inner wall of the lumen near the sphincter by the stent may prevent the lumen from becoming completely occluded when the sphincter contracts.

A pulsating blood vessel is another example of a body lumen whose diameter changes dynamically over time where it is often desired to place a stent. Endovascular grafts are composed of a stent or stent-like scaffolding integrated with graft material. Inaccurate graft sizing and the inability of a graft to dynamically adjust to changes in the aorta's diameter during systole and diastole can result in the passage of fluid in the aneurysm between the vessel wall and the graft (endo-leaks), which can result in aneurysm expansion and rupture. An endo-leak is caused by incomplete exclusion of the aneurysm from the arterial circulation by the stent. Endo-leaks are a common complication, occurring in as many as 45% of patients undergoing stent-graft for Abdominal Aortic Aneurysm (AAA) repair.

The lumen of a peristaltic organ is yet another example of a body lumen whose diameter changes dynamically over time where it is often desired to place a stent. However, the presence of a stent in a peristaltic organ may interfer with the propagation of the peristaltic waves. In such cases, peristaltic waves are unable to traverse the stent, thus preventing peristalsis downstream to the stent.

SUMMARY OF THE INVENTION

The present invention provides an endoluminal device for insertion into a body lumen whose diameter changes dynamically over time. As explained above, such body lumens include a pulsating artery, a peristaltic organ, or a lumen adjacent to a sphincter. The device, referred to herein as a "lining", is generally cylindrical in shape, and when positioned in the lumen, lines the lumen wall. In accordance with the invention, the lining is elastic and generally cylindrical in shape, having a cross-sectional area allowing it to conform to the cross-sectional shape of the lumen. Thus, for example, the lining may have a circular, triangular, or irregular cross-sectional shape, as required in any application. The lining has an unstrained caliber slightly larger than the maximal caliber of the body lumen in which it is to be deployed. The caliber of the lining decreases when radially inward forces are applied to the device as the lumen constricts. As described in detail below, the lining is structured so as to prevent it from collapsing when its caliber is decreased. Due to the elastic character of the lining, when the radial forces are removed, the lining returns to its unstrained caliber. Therefore, when the device of the invention is inserted into the body lumen, the device continuously conforms to the shape of the lumen as the caliber of the lumen fluctuates dynamically over time. The surface of the lining may be continuous, for example, either by embedding the elastic elements of the lining in a flexible material or covering the elastic elements in a flexible cylindrical sheath.

The lining of the invention may be used in conjunction with a stent. For example, use of lining of the invention adjacent to a stent eliminates the sharp pressure gradient that otherwise exists on the lumen wall around the ends of the stent. A region of a steep pressure gradient is known to induce ingrowth of tissue at the ends of the stent that partially or completely occludes the lumen at the ends of the stent.

The lining of the invention may be positioned in a lumen adjacent to a sphincter. Adjacent to the lining, a stent may be positioned in the lumen, so that the lining is flanked on one side by the sphincter and the other side by the stent. The lining and the stent may be fabricated as a single unit or may be formed as two separate units that are joined together before insertion into the lumen and inserted together as a single integral unit, or the lining and stent may be inserted separately. The stent maintains the patency of the lumen in a region that is separated from the sphincter by the lining. When the sphincter contracts, and the diameter of the lumen adjacent to the sphincter decreases, the diameter of the lining also decreases while conforming to the shape of the lumen wall. When the sphincter relaxes, and the diameter of lumen adjacent to the sphincter increases, the diameter of the lining also increases while conforming to the shape of the lumen wall. The lining thus dynamically conforms to the lumen shape adjacent to the sphincter during opening and closing of the sphincter.

Use of the lining in conjunction with a stent in a lumen adjacent to a sphincter has several advantages. First, it allows the stent to be more accurately positioned in a lumen near a sphincter. The distance between the sphincter and a region of the lumen in need of a stent is measured, and a lining in accordance with the invention is used having a length equal to this distance. The stent and the lining are then positioned as explained above. The presence of the lining near the sphincter also provides some support to the lumen wall adjacent to the sphincter without interfering with the functioning of the sphincter.

When a stent, or a graft containing a stent, is to be inserted into a pulsating artery such as the aorta, the graft or stent is used in conjunction with one or two linings of the invention. The stent or graft is positioned in the artery flanked by a lining of the invention at either one or both ends. The lining or linings expand during the increase in the caliber of the artery that occurs during systole, and contract during the decrease in the caliber of the artery that occurs during diastole. By dynamically conforming to the caliber of the vessel wall, flow of fluid between the stent or graft and the vessel wall is prevented.

A lining in accordance of the invention may be used in conjunction with two stents in the lumen of a peristaltic organ such as the ureter, intestines or esophagus. The lining is positioned in the lumen flanked by a stent at each end. A stent is used which, on the one hand, is strong enough to tutor the lumen, sufficiently compliant not to block propagation of peristaltic waves. Due to the elastic nature of the lining, it does not interfere with the propagation of peristaltic waves.

Thus, in its first aspect, the invention provides a cylindrical lining for insertion into a body lumen having a fluctuating caliber, the lining having a radial resistance less than a radial force applied to it by the lumen as the caliber of the lumen fluctuates so as to allow the lining to continuously conform to the shape of the lumen.

In its second aspect, the invention provides a method for treating a body lumen comprising inserting into the lumen a cylindrical lining having a radial resistance less than a radial force applied to it by the lumen as the caliber of the lumen fluctuates so as to allow the lining to continuously conform to the shape of the lumen.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1 shows a lining in accordance with one embodiment of the invention;

FIG. 2 shows a lining integral with a stent;

FIG. 3 shows device comprising two linings of the invention;

DETAILED DESCRIPTION OF THE INVENTION

Figure 4A:
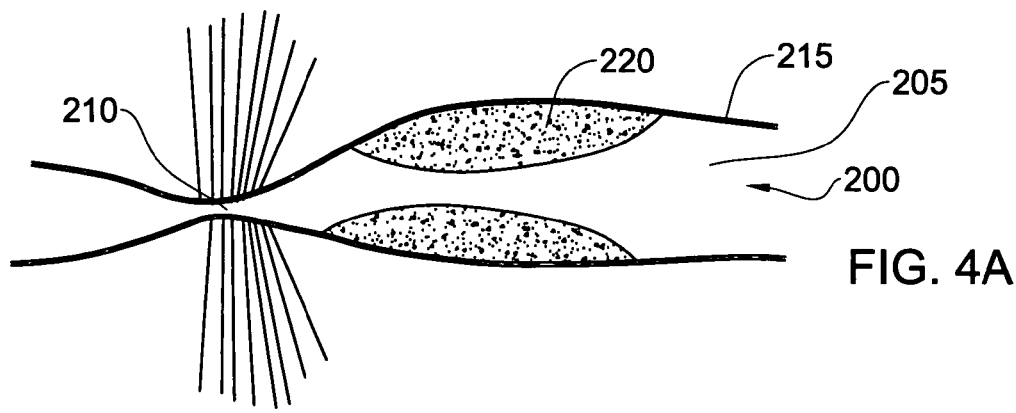
FIG. 4 shows deployment of the device of FIG. 2 in a body lumen.

FIG. 1a shows a lining in accordance with one embodiment of the invention. The lining, generally indicated by 10, is formed from a resilient filament 15 that has been fashioned into an undulating helix. The filament may be made of spring steel, a super-elastic shape memory alloy such as Nitinol, or a shape memory alloy. The lining is shown in FIG. 1a in its unstrained conformation. When a radially inward force is applied to the lining 10, the lining 10 constricts while maintaining its generally cylindrical shape, as shown in FIG. 1b. As the lining 10 constricts, the surface density of the filament 15 in the wall of the lining 10 increases. Due to the resilient nature of the filament 15, when the radially inward forces are removed from the lining, the lining returns from the small caliber configuration shown in FIG. 1b to its large, unstrained caliber shown in FIG. 1a.

The lining 10 is dimensioned so as to have an unstrained large caliber that is slightly larger than the maximal caliber of the body lumen in which it is to be deployed. The resistance of the lining to inward radially applied forces is determined by such factors as the gauge of the filament 15 and the extent to which the geometric structure into which it has been fashioned is convoluted. Thus, for the lining 10, a desired resistance may be imparted by an appropriate selection of the values of these factors. In practice, the elastic resistance of the lining 10 is determined to be less than the radially inward force applied to it by the lumen wall in which it is to be deployed when the lumen constricts.

In order to deploy the lining of the invention in a body lumen, the lining may be maintained in a small caliber by inserting it into a restraining sleeve. The lining and sleeve are then delivered to the site of deployment by means of a catheter. After correct positioning of the lining, the restraining sleeve is removed, and the caliber of the lining increases so as to conform to the caliber and form of the lumen in which it is deployed. As the caliber of the lumen fluctuates dynamically over time, the lining continuously conforms to the caliber and shape of the lumen.

FIG. 2A shows a lining 110 of the invention that is integral with a stent 103. The stent 103 may be any stent known in the art. In a preferred embodiment, the lining 110 is formed from a filament 105 and the stent 103 is formed from a filament 106. The filaments 105 and 106 are made from a resilient material such as spring steel or a shape-memory alloy, as described above in reference to FIG. 1. The filaments 105 and 106 have been fashioned into undulating helices. The filament 105 and its geometric structure are selected so as to impart to the lining 110 a radial resistance that allows it to conform to the caliber of the lumen as it dynamically fluctuates over time, as explained above in reference to the lining of FIG. 1. The filament 106 and its geometrical structure are selected so as to impart to the stent 103 a radial resistance that allows it to withstand radial forces exerted on it by the lumen wall. In the embodiment shown in FIG. 2a, the undulating helices of the lining 110 and the stent 103 have the same geometrical structure However, the filament 105 has a smaller gauge than the filament 106. For example, filament 106 can be made of a super elastic Nitinol wire 0.3 mm in diameter, while the end segment 110 can be made of the same alloy wire with a diameter of 0.2 mm.

FIG. 2b shows another embodiment of the invention in which a lining 120 is integral with a stent 123. The lining 120 is formed from a filament 125 and the stent 123 is formed from a filament 126. The filaments 125 and 126 are made from a resilient material such as spring steel or a shape-memory alloy, as described above in reference to FIG. 1. The filaments 125 and 126 have been fashioned into undulating helices. As with the embodiment shown in FIG. 2a, the filament 125 and its geometrical structure are selected so as to impart to the lining 120 a radial resistance that allows it to conform to the caliber of the lumen as it dynamically fluctuates over time, as explained above in reference to the lining of FIG. 1. The filament 126 and its geometrical structure are selected so as to impart to the stent 123 a radial resistance that allows it to withstand radial forces exerted on it by the lumen wall. In the embodiment shown in FIG. 2b, the filaments 125 and 126 have the same gauge. However, the filament 126 has been fashioned into a geometric structure that is more convoluted than that of the filament 125.

FIG. 3 shows a device 135 comprising two linings 130a and b of FIG. 2a in accordance with the invention. The lining 130b is integral with a stent 133. The linings 130a and b are tethered to each other by means of a tether 135. As shown in FIG. 4d below, the device shown in FIG. 3 is positioned in a lumen adjacent to a sphincter with the linings 130a and b on opposite sides of the sphincter.

Figure 4B:
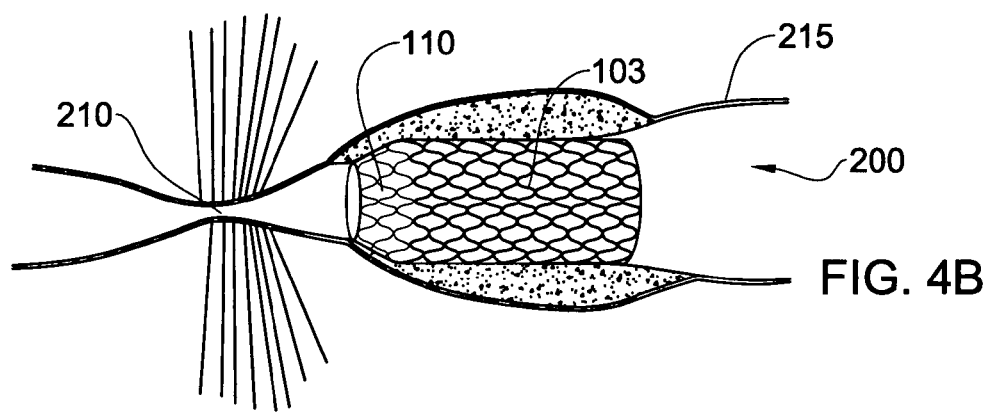
Figure 4C:
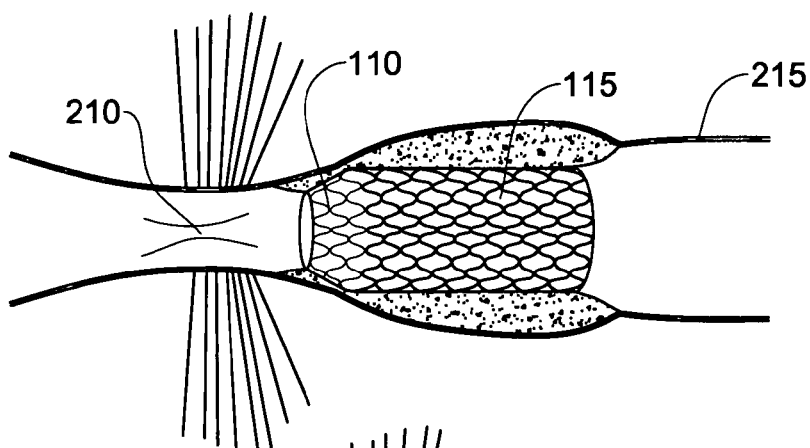
Figure 4D:
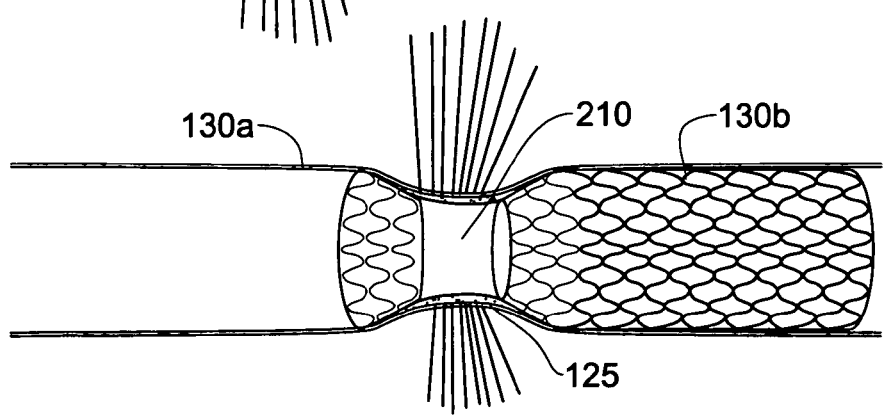

FIG. 4A shows a body lumen 200 of a hollow organ 205, including obstructing tissue 220, near a sphincter 210, and FIG. 4B shows the device 100 after deployment in the lumen 200. The stent 103, applies radially on the wall of the organ so as to maintain patency of the lumen. The lining 110 is proximal to the sphincter. In FIG. 4B, the sphincter 210 is closed and the lining 110 conforms to the lumen's smaller caliber near the sphincter providing the maximum allowable radial support without interfering with the sphincter function of closing the lumen. FIG. 4C shows the sphincter 210 in an open state where the lining 110 is expanded following the lumen's enlarged diameter proximal to the sphincter.

FIG. 4d shows the device of FIG. 3 after positioning in a lumen adjacent to a sphincter 210. The linings 130a and 130b are located on opposite sides of the sphincter 210. The tether 125 passes through the sphincter 210. The lining 130a functions as an anchor that prevents the lining 130b and the stent 133 from migrating away from the sphincter 210, while not interfering with the activity of the sphincter.

Figure 5A:
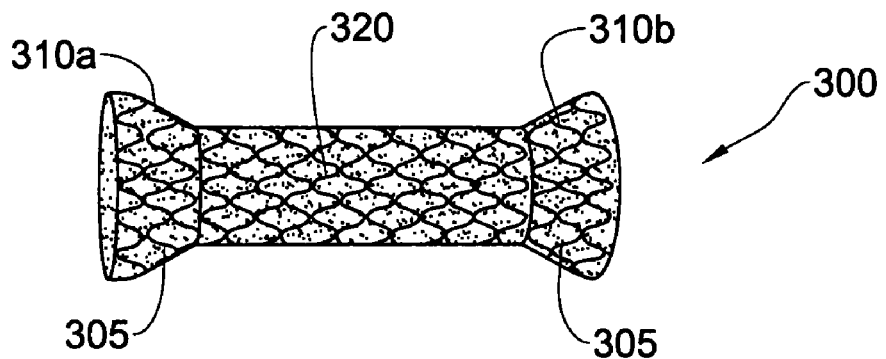
FIG. 5 shows a device comprising a stent flanked by two linings of the invention.
Figure 5B:
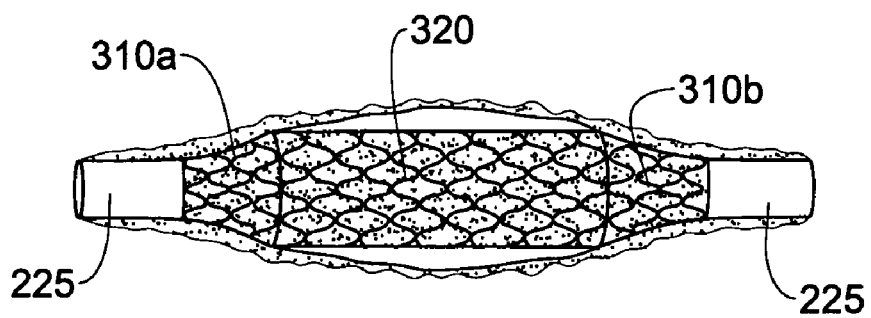
Figure 5C:
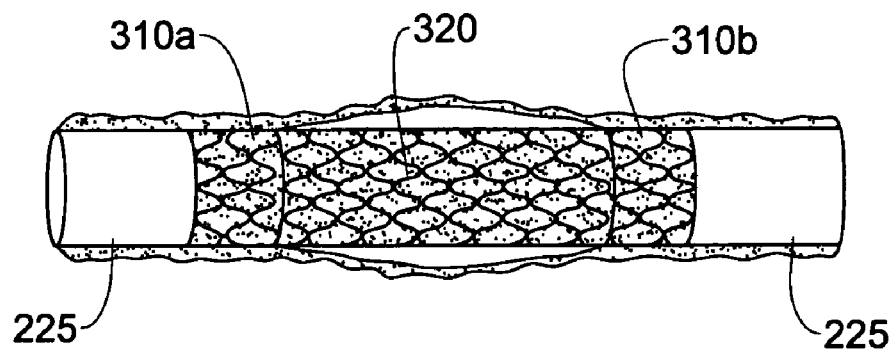

FIG. 5a shows a device 300 comprising a lining in accordance with another embodiment of the invention. The device 300 is adapted for placement in a pulsating vessel such as an aorta. The device 300 has two linings 310a and b in accordance with the invention, integral with a stent 320, and flanking the stent. The two linings 310a and b have an unstrained caliber slightly larger than the maximal caliber of the lumen. In the device 300, spaces between parts of the filament are filled with a bio-stable polymeric membrane 305. FIGS. 5b and 5c show the device 300 after placement in a lumen having pulsating walls 225, such as an aorta or digestive tract organ. In FIG. 5b, the lumen is shown having a small caliber, while in FIG. 5c, the lumen is shown having a large caliber. For example, in the case that the lumen is an artery, FIGS. 5b and 5c would correspond to diastole and systole, respectively. As shown in FIGS. 5b and 5c, the linings 310a and b remain in contact with the lumen walls 225 as the walls pulsate. During systole, the upstream lining 310a expands with the expansion of the artery adapting itself snugly to the wall of the artery. The presence of the membrane 305 prevents fluids, such as blood, from coming in between the stent 320 and the lumen walls 225.

Figure 6:
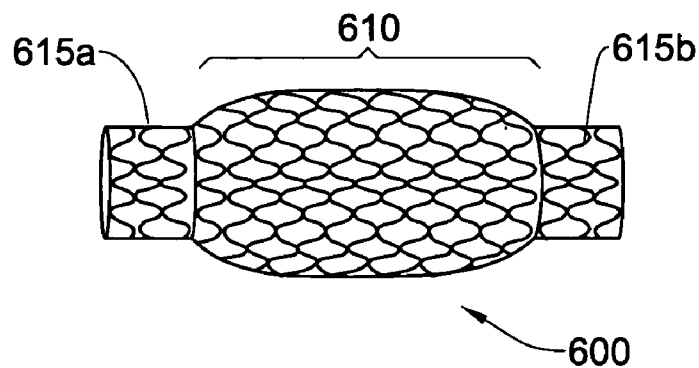
FIG. 6 shows a lining of the invention flanked by two stents.

FIG. 6 shows a device 600 comprising a lining 610 in accordance with the invention that is integral with two stents 615a and b. The two stents 615 are located at the ends of the device 600, flanking the lining 610. The device 610 may be used in a peristaltic organ such as the esophagus. The stents 615 are designed to be sufficiently short so as not to block propagation of the peristaltic wave. The lining 610 is designed to be strong enough to tutor the lumen in the absence of peristaltic waves, while sufficiently compliant not to block propagation of peristaltic waves.

Figure 7A:
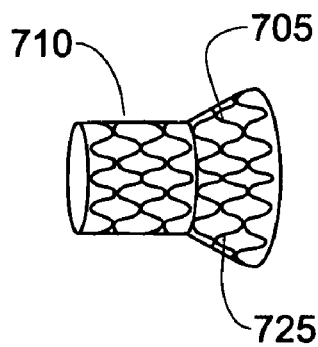
FIG. 7 shows a lining integral with a stent.
Figure 7B:
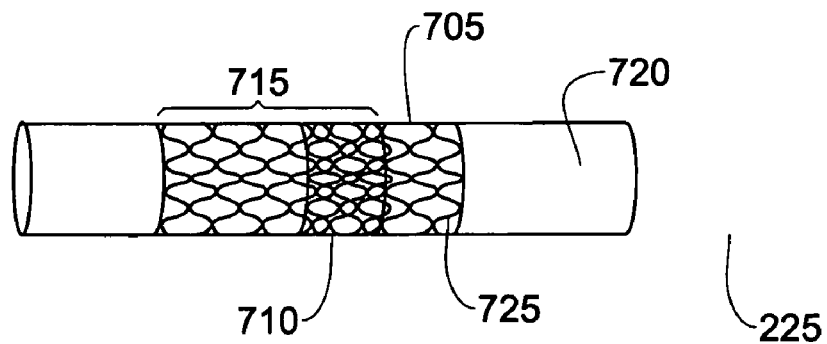

FIG. 7a shows a device 700 comprising a lining 705 that is integral with a stent 710. The device 700 may be used to adding a lining to previously implanted stent. As shown in FIG. 7b, the stent 710 is dimensioned to be expandable within the lumen of a stent 715 that was previously implanted in the body lumen 720. The lining 705 is configured to have an unstrained caliber slightly larger than the largest caliber of the lumen 720. As stated above, positioning the lining 705 adjacent to the stent 715 eliminates the sharp pressure gradient that previously existed on the wall of the lumen 720 around the ends of the stent. A region of a steep pressure gradient is known to induce ingrowth of tissue at the ends of a stent that partially or completely occludes the lumen at the ends of the stent. The lining 705 may be surrounded by a flexible material 725 in order prevent fluids from entering between the stent 715 and the wall of the lumen 720.

The invention claimed is:
1. A device for insertion into a body lumen having a fluctuating caliber, the device comprising:
    a cylindrical lining having a radial resistance less than a radial force originated by the body and applied to the lining by the lumen as the caliber of the lumen fluctuates so as to allow the lining to continuously conform to the shape of the lumen; and a stent withstanding all radial forces originated by the body and exerted on the stent by the lumen wall such that the caliber of the stent does not decrease after deployment into the lumen, wherein (1) the cylindrical lining is tapered at least at one end on an inner and an outer surface of the cylindrical lining such that a thickness of the lining between the inner and outer surfaces is uniform along the taper, (2) the lining and the stent form a continuous tubular structure, (3) a thickness of the stent is of equal thickness as that of the lining, (4) the thickness of the stent is uniform across its length, (5) the lining is formed from a resilient film fashioned into an undulating helix and (6) spaces between parts of the filament are filled with a bio-stable polymeric membrane.

2. The device according to claim 1, wherein the stent is flanked by two of the linings.

3. A method for treating a body lumen comprising inserting into the lumen the device according to claim 2.

4. The method according to claim 3 wherein the lumen is adjacent to a sphincter.

5. The method according to claim 3 wherein the lumen is a pulsating artery or a peristaltic organ.

6. The device according to claim 1, wherein the lining is flanked by two of the stents.

7. A method for treating a body lumen comprising inserting into the lumen the device according to claim 6.

8. The method according to claim 7 wherein the lumen is adjacent to a sphincter.

9. The method according to claim 7 wherein the lumen is a pulsating artery or a peristaltic organ.

10. The device according to claim 1, further comprising two of the linings joined by a tether.

11. An endovascular graft comprising the device according to claim 1.

12. The device of claim 1, wherein the lining includes elastic elements that are embedded in or surrounded by a flexible material.

13. The device according to claim 1, wherein the entire length of the cylindrical lining has a radial resistance less than a radial force originated by the body and applied to the lining by the lumen as the caliber of the lumen fluctuates so as to allow the lining to continuously conform to the shape of the lumen.

14. The device according to claim 1, wherein the filament is made from at least one of spring steel and shape memory alloy.

15. A method for treating a body lumen comprising inserting into the lumen the device according to claim 1.

16. The method according to claim 15 wherein the lumen is adjacent to a sphincter.

17. The method according to claim 15 wherein the lumen is a pulsating artery or a peristaltic organ.

18. A method for treating a body lumen in which a stent has been implanted, comprising:
inserting into a lumen the device according to claim 1, wherein the lining of the device has an unstrained caliber larger than a maximum caliber of the lumen and the stent of the device is configured to be expandable within a lumen of the previously implanted device.

19. The method according to claim 18 wherein the lumen is adjacent to a sphincter.

20. The method according to claim 18 wherein the lumen is a pulsating artery or a peristaltic organ.

* * * * *